(12) United States Patent
Brodbeck

(10) Patent No.: US 10,039,620 B2
(45) Date of Patent: Aug. 7, 2018

(54) CERAMIC BODY, IN PARTICULAR FOR USE AS A DENTAL IMPLANT

(71) Applicants: Markus Schlee, Forchheim (DE); Holger Zipprich, Malchen (DE); Urs Brodbeck, Erlenbach (CH)

(72) Inventor: Urs Brodbeck, Erlenbach (CH)

(73) Assignees: Markus Schlee, Forchheim (DE); Holger Zipprich, Malchen (DE); Urs Brodbeck, Erlenbach (CH)

(*) Notice: Subject to any disclaimer, the term of this patent is extended or adjusted under 35 U.S.C. 154(b) by 0 days.

(21) Appl. No.: 14/765,562

(22) PCT Filed: Feb. 5, 2014

(86) PCT No.: PCT/EP2014/052272
§ 371 (c)(1),
(2) Date: Aug. 3, 2015

(87) PCT Pub. No.: WO2014/122189
PCT Pub. Date: Aug. 14, 2014

(65) Prior Publication Data
US 2015/0359613 A1    Dec. 17, 2015

(30) Foreign Application Priority Data
Feb. 5, 2013 (DE) .................. 10 2013 201 885

(51) Int. Cl.
*A61C 8/00* (2006.01)
*A61C 19/06* (2006.01)
*A61K 6/02* (2006.01)

(52) U.S. Cl.
CPC ............ *A61C 8/0013* (2013.01); *A61C 19/06* (2013.01); *A61K 6/024* (2013.01); *A61K 6/0205* (2013.01)

(58) Field of Classification Search
CPC ....... A61C 8/00; A61C 8/0015; A61C 8/0013; A61C 8/0012; A61C 19/06; A61K 6/02;
(Continued)

(56) References Cited

U.S. PATENT DOCUMENTS 3,420,760 A    1/1969   Bernard
4,321,042 A *  3/1982   Scheicher ............ A61C 8/0012
                                                           106/35
(Continued)

FOREIGN PATENT DOCUMENTS

DE    202004009059 U1   9/2004
DE    102010017886 A1   3/2012
(Continued)

OTHER PUBLICATIONS

"Applied Superconductivity: Metallurgy and Physics of Titanium Alloys." Cryogenics 26.12 (1986): 704. Www.nde-ed.org. Eddy Current Technology.*
(Continued)

*Primary Examiner* — Nicholas Lucchesi
*Assistant Examiner* — Shannel Wright
(74) *Attorney, Agent, or Firm* — Suzannah K. Sundby, Esq.; Canady + Lortz LLP

(57) ABSTRACT

A ceramic body (20) for use in a bone implant, in particular in a dental implant (24), shall be suitably upgraded for the utilization of an electrolytic cleaning and treatment concept. For this purpose, the ceramic body (20) according to the invention has, in a surface area (40) intended for contact with human tissue, a specific electric resistance of maximally $10^{-2}$ Ωcm.

11 Claims, 2 Drawing Sheets

(58) Field of Classification Search
CPC .................. A61K 6/0205; A61K 6/024; A61F 2002/2821; A61F 2002/30668; A61F 2002/30052
See application file for complete search history.

(56) References Cited

U.S. PATENT DOCUMENTS

| | | | | |
|---|---|---|---|---|
| 4,351,069 | A * | 9/1982 | Ballintyn | A61C 8/0013 156/77 |
| 5,064,731 | A * | 11/1991 | Miyazaki | A61C 13/00 106/1.13 |
| 5,695,337 | A * | 12/1997 | Tyszblat Sadoun | A61C 8/0048 433/173 |
| 6,165,925 | A * | 12/2000 | Rieger | A61L 27/10 433/201.1 |
| 8,075,312 | B2 * | 12/2011 | Collins | A61C 8/0006 433/173 |
| 8,241,030 | B2 * | 8/2012 | Vieillot | B29C 49/12 264/519 |
| 8,602,782 | B2 * | 12/2013 | Lomicka | A61C 8/0012 433/174 |
| 8,684,734 | B1 * | 4/2014 | Lyren | A61L 27/06 433/173 |
| 2003/0146108 | A1 | 8/2003 | Nakamura | |
| 2003/0153965 | A1 * | 8/2003 | Supronowicz | A61C 8/0007 607/116 |
| 2003/0176927 | A1 * | 9/2003 | Steinemann | A61F 2/30767 623/23.55 |
| 2005/0012231 | A1 * | 1/2005 | Olsson | A61L 27/42 264/19 |
| 2005/0079201 | A1 | 4/2005 | Rathenow et al. | |
| 2005/0106534 | A1 * | 5/2005 | Gahlert | A61C 8/0012 433/173 |
| 2005/0181330 | A1 * | 8/2005 | Kim | A61C 8/0069 433/173 |
| 2006/0105297 | A1 * | 5/2006 | Knapp | A61C 13/0003 433/206 |
| 2006/0265026 | A1 * | 11/2006 | Madjar | A61C 8/0006 607/51 |
| 2009/0092943 | A1 * | 4/2009 | Tamir | A61C 8/0012 433/172 |
| 2009/0258327 | A1 * | 10/2009 | Zipprich | A61C 8/0012 433/173 |
| 2010/0241229 | A1 * | 9/2010 | Baehre | A61B 17/00491 623/16.11 |
| 2011/0003083 | A1 * | 1/2011 | Yang | A61F 2/30767 427/453 |
| 2011/0052834 | A1 * | 3/2011 | Lenz | A61C 8/0013 427/535 |
| 2011/0065064 | A1 * | 3/2011 | Kahdemann | A61C 8/0012 433/174 |
| 2011/0183281 | A1 * | 7/2011 | Jensen | A61C 7/20 433/18 |
| 2011/0318708 | A1 * | 12/2011 | Gahlert | A61C 8/0012 433/174 |
| 2012/0064486 | A1 * | 3/2012 | Sobrado Marinho | A61B 5/228 433/173 |
| 2012/0276501 | A1 * | 11/2012 | Terkel | A61C 8/0007 433/173 |
| 2013/0001086 | A1 * | 1/2013 | Yamashita | C01G 23/047 205/50 |
| 2013/0199361 | A1 | 8/2013 | Lenz | |
| 2013/0236854 | A1 * | 9/2013 | McEntire | A61C 8/0013 433/173 |
| 2015/0282907 | A1 | 10/2015 | Zipprich et al. | |
| 2016/0000947 | A1 * | 1/2016 | Brodbeck | A61L 2/0011 205/705 |
| 2016/0015483 | A1 * | 1/2016 | Kumar | A61C 8/0012 606/301 |
| 2016/0021889 | A1 | 1/2016 | Zipprich et al. | |

FOREIGN PATENT DOCUMENTS

| | | |
|---|---|---|
| DE | 102012022593 B3 | 3/2014 |
| JP | H08-299999 A | 11/1996 |
| JP | 2006-501867 A | 1/2006 |
| JP | 2008-214591 A | 9/2008 |
| WO | 2003045268 A1 | 6/2003 |
| WO | 2006006923 A1 | 1/2006 |
| WO | 2008011948 A1 | 1/2008 |
| WO | 2010139762 A1 | 12/2010 |
| WO | 2012045830 A1 | 4/2012 |

OTHER PUBLICATIONS

Yildiz, A, et al. "Electric Properties of TiO2 Thin Films." Researchgate, Elsevier: Journal of Non-Crystalline Solids, Aug. 18, 2008, www.researchgate.net/publication/256772430_Electrical_properties_of_TiO2_thin_films.*
"Titanium Dioxide—Titania (TiO2)", Azo Materials, https://www.azom.com/properties.aspx?ArticleID=1179M.*
"International Search Report received in PCT/EP2014/052271", dated May 20, 2014.
"International Search Report received in PCT/EP2014/052272", dated May 8, 2014.
"International Search Report received in PCT/EP2014/052270", dated May 12, 2014.
"English Translation of International Preliminary Report on Patentability received in PCT/EP2014/052272, dated Aug. 13, 2015".
Office Action received in JP 2015-555757 dated Jan. 9, 2018.

* cited by examiner

CERAMIC BODY, IN PARTICULAR FOR USE AS A DENTAL IMPLANT

BACKGROUND OF THE INVENTION

1. Field of the Invention

The invention relates to a ceramic body, in particular for use in a bone implant, in particular as a dental implant. It also relates to a bone implant, in particular a dental implant, with such a ceramic body.

2. Description of the Related Art

Bone implants and, in particular dental implants, are known in a multitude of forms. Dental implants are mostly inserted into the jawbone by screwing it in, in the place of an extracted or shed tooth, in order to fix there, after a healing-in phase of about three to four months, a prosthetic superstructure part or a crown serving as a denture piece. For this purpose, such a dental implant, as well as a bone implant in general, is usually designed as a suitably shaped metallic or ceramic body and formed in the manner of a pivot, whose apical end is provided with a screw thread, mostly a self-cutting screw thread, with which the pivot is inserted into the correspondingly prepared implant bed.

As a rule, dental implants are made of titanium, zirconium, niob, or tantalum, or of tissue-compatible alloys containing one of these elements as main constituent. Furthermore, dental implants are also made of ceramics. The ceramics used are mostly ceramics based on zirconium oxide, in which the tetragonal phase is preferably stabilized by means of adding yttrium oxide (TZP, TZP-A with shares of aluminium oxide), or which are aluminium-oxide reinforced by, mostly additionally, adding aluminium oxide (ATZ ceramics). Dental implants based on aluminium oxide are, however, also known.

A treatment element, in particular for use with an implant part, as well as a method for cleaning a dental-implant part, are known from the German patent application with the reference number 10 2012 022 593.8, not prior published, whose entire disclosure is incorporated by reference. Such a cleaning of an implant part can be desirable or necessary to guarantee the preservation of the inserted implant in the bone substance. In fact, a biofilm may form on the firm surface of implants, enclosed by tissue and tissue liquid, which biofilm is colonized by bacteria which may finally lead to chronic and recurrent infections. This syndrome is called, in the case of dental implants, periimplantitis. In particular in the dental area, similar to periodontitis, a combination of neglected mouth hygiene, adhesion of a biofilm on the usually microrough surface of the post part, and other factors lead to the full picture of periimplantitis, which is characterized by an increasing charge and destruction of the hard and soft tissues. The areas where the hard and/or soft tissues retreat are usually covered by a biofilm.

SUMMARY OF THE INVENTION

The cleaning method described in the above-mentioned application is based on the concept, to kill and remove the biofilm or the germs forming the contamination, starting from the implant surface, without damaging the implant surface. For this purpose, an electrolytic process is provided, by which the ions (cations and/or anions) are conveyed by means of electrostatic forces through the biofilm. These ions react chemically or electrochemically on the implant surface. Through these reactions, new compositions of matter are created and/or the ions themselves and/or parts of these ions are converted into the atomic state. Furthermore, it is also possible that the ions react with the surface material (e.g. development of an oxide layer or erosion of material).

The germicidal effect of this process is based on different effects. On the one hand, ions from the biofilm itself (and also from the bacteria) are transported to the anode or cathode through the application of an electric voltage. This may lead to a killing of bacteria and viruses. Furthermore, the ions, while passing through the biofilm, may undergo biochemical reactions, which may also lead to a killing of bacteria and/or viruses. Another possibility of killing consists in that the compositions of matter newly formed on the implant surface possess an antibacterial and/or antiviral and/or antifungal effect. This may, of course, also happen when the ions are converted into the atomic state.

The treatment element described in the above-mentioned application is specifically designed for performing this cleaning method directly on the inserted dental implant, i.e. preferably while the post part is anchored in the bone in the patient's mouth. For this purpose, it is provided to directly connect the treatment element with the inserted post part and to then supply a suitable treatment liquid, which can serve as a basis for the desired electrolytic process when an electric current is applied, in the immediate vicinity of the inserted post part into the afflicted space area of the adjacent bone substance and to charge it with the electric current. The application of this treatment element makes it, however, necessary to establish both a mechanical and an electric contact with the inserted post part.

The present invention is based on the problem to provide a ceramic body suitable for use in a bone implant, in particular in a dental implant, which is suitably upgraded for the utilization of the cleaning and treatment concept described in the above-mentioned patent application. Furthermore, a bone implant, in particular a dental implant, which is particularly suitable for the utilization of the cleaning and treatment concept described in the above-mentioned patent application and which includes such a ceramic body shall be provided.

With regard to the ceramic body, this problem is solved according to the invention by the fact that said ceramic body has, in a surface area intended for contact with human tissue, a specific electric resistance of maximally $10^{-2}$ $\Omega$cm.

Advantageous embodiments of the invention are the subject matter of the dependent claims. Further and/or alternative advantageous embodiments of the invention are also obvious from the description of the figures.

The invention starts out on the consideration that an electrolytic treatment and cleaning of the ceramic body from a biofilm is made possible by specifically upgrading said ceramic body for the charging with current, which is necessary for that purpose. Therefore, it should be designed in a suitably conductive manner, especially in the surface areas where the electrolytic decomposition of the treatment liquid shall be effected.

To achieve this, generally different approaches come into question. On the one hand, the ceramic body can completely be made of an electrically sufficiently conductive or an electrically semiconductive ceramic.

Alternatively, the ceramic body can be provided, in the surface area intended for the contact with human tissue, with an electrically conductive coating. Advantageously, such a coating is formed by a metal, by an electrically conductive synthetic material and/or by an electrically conductive carbon, or, particularly preferably, by a doped ceramic, preferably indium oxide and/or indium-tin oxide, zinc oxide, silicon nitrite, $MoSi_2$, $Si_3N_4$—$MoSi_2$—$SiC$, $ZrO_2/CaO$, $Al_2O_3/TiN$, $BaTiO_3$, a silicide, a nitride, a ceramic containing titanium, and/or a titanate. As metallic coating, for example platinum, gold, titanium, etc. can be used. A metallic coating might, however, in case of the preferred use in a dental implant, be suitable to a certain extent only, for aesthetic, biological or allergological reasons. Contrary to that, the particularly preferred electrically conductive or electrically semiconductive ceramics might be able, especially when used in a dental implant, with a corresponding coloring of the coating, to comply with the aesthetic, biological or allergological requirements.

A fully ceramic dental implant (superstructure part/post part), which is not electrically conductive itself, can be coated with such an electrically conductive or electrically semiconductive ceramic. This coating can be applied completely/on the entire part or in partial areas only. Electric contacting is preferably effected via the implant shoulder. For this purpose, it would be favorable to make the coating thickness thicker at the contacting place in the area of the implant shoulder, e.g. two, five, ten times thicker. If the outside as well as the inside of an implant would be coated in such a manner, an electric contacting would also be possible via the inside of the implant.

In the case of an anodic switching of titanium implants, in particular made of titanium grade IV or purer titanium, a titanium-oxide layer will form, which directly after its formation will very greatly reduce or prevent the electrochemical processes on the surface, unless the electric voltage is increased. Therefore, an anodic energization for cleaning purposes is possible for a very short time or a single time only without endangering the patient through the electric voltage. If such a titanium implant is coated with an electrically conductive or electrically semiconductive ceramic, the growth of titanium oxide under anodic energization can be prevented. In this way, it would be possible to use the anodic energization for cleaning the implant surface over a long duration. Another advantage of such a surface would be the fact that no metal ions could be detached from the metallic implant.

Furthermore, it is also imaginable to add an electrically conductive or semiconductive material, preferably based on ceramic and/or carbon, to a non-electrically conductive ceramic which is suitable as an implant module, to produce an electric conductivity or electric semiconductivity.

It is particularly preferred to use the ceramic body for a bone implant, in particular as part of a dental implant. The latter can then be electrically contacted for cleaning purposes either occlusally or via the interior. Of course, it is also possible to use an electric contacting via a cleaning cannula from outside.

With regard to the bone implant, the above-mentioned problem is solved by designing said implant as a ceramic body of the above-mentioned type. In an embodiment as dental implant, the latter comprises according to the invention a post part anchorable in a jawbone and a superstructure part associated therewith, the post part being designed as a ceramic body of the above-mentioned type. The dental implant can be designed as a so-called single-piece implant, in which the post part and the superstructure part are parts of a common integral base body. Alternatively, the dental implant can, however, also be designed in several parts, in the sense that the post part, on the one hand, and the superstructure part, on the other hand, are component parts which are independent of each other and can be joined by means of a suitable connection. The superstructure part can be provided in particular for fixing a denture piece thereon.

Advantageously, the post part is designed as a ceramic body based on yttrium-oxide-stabilized and/or aluminium-oxide-stabilized zirconium oxide. To particularly promote the growing into the jawbone, the post part is advantageously additionally provided with a particularly suitable surface. For this purpose, preferably its surface area intended for the contact with human tissue is provided, at least in a partial area, with a structure including nanoscopic pores or with a structure otherwise nanoscopically configured, and has a depletion zone based on yttrium-oxide-stabilized and/or aluminium-oxide-stabilized zirconium oxide with a reduced share of yttrium oxide or aluminium oxide, as compared with the inner volume.

The advantages achieved with the invention consist in particular in the fact that through the design of the ceramic body with a sufficiently conductive surface, a body of such a design can also be subjected to the treatment and cleaning method described in the above-mentioned patent application. For a ceramic body, too, in particular for a ceramically designed bone implant or dental implant, a reliable removal of the biofilm is possible with high local precision, even from locally limited space areas of the body concerned. For this purpose, the cleaning concept of electrolytic germ killing, recognized as particularly effective, can reliably be applied. Especially in case of an only limited bacterial infestation of the object needing treatment, this cleaning can be effected in a particularly need-based manner, and in case of a treatment of an inserted dental implant, this cleaning can even be effected without having to remove the prosthetics or possibly the abutment.

DESCRIPTION OF THE DRAWINGS

An exemplary embodiment of the invention is explained in detail by means of a drawing, in which.

DETAILED DESCRIPTION OF THE INVENTION

The basic principle of the invention is explained in the following by means of the treatment system 1 shown in FIG. 1. Of course, alternatively or additional, however, it is also possible to use a treatment system described in the German patent application with the reference number 10 2012 022 593.8, not prior published, whose entire disclosure is incorporated by reference.

Figure 1:
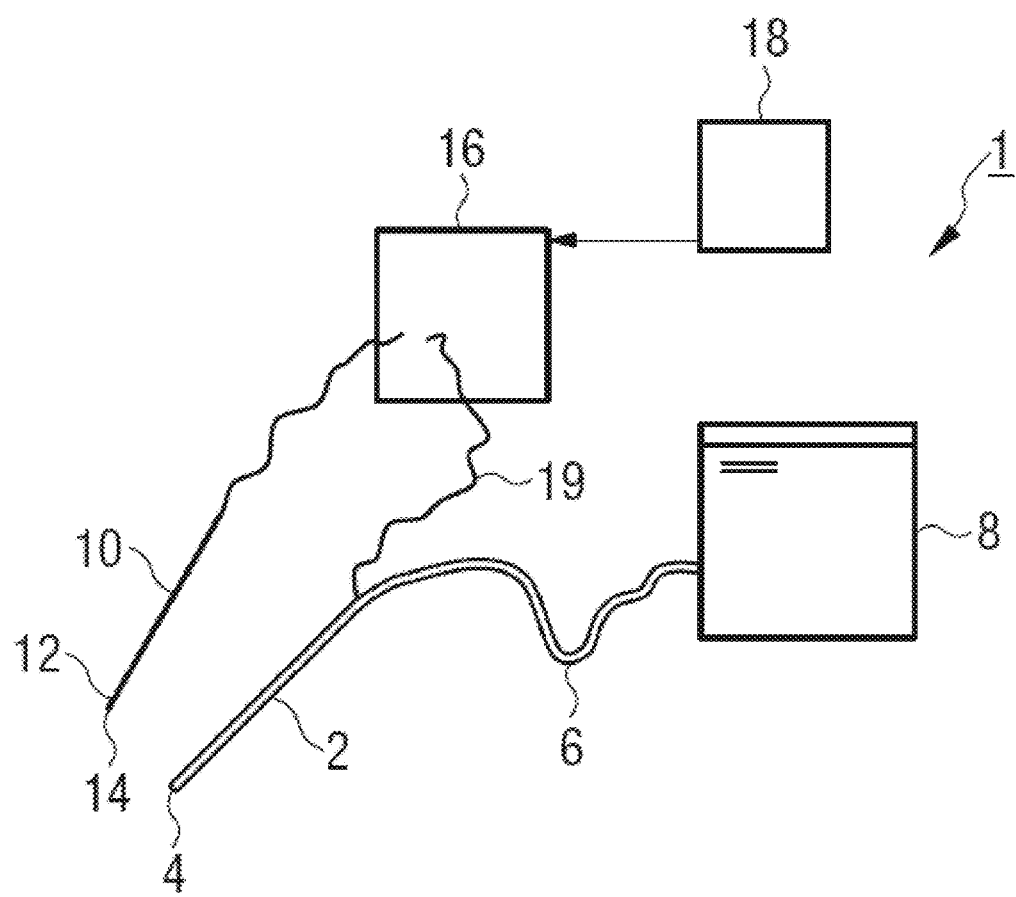
FIG. 1 shows a treatment system for cleaning a component contaminated with a biofilm.

The treatment system 1 according to FIG. 1 is provided for cleaning a component part contaminated with a biofilm, in particular an implant part. The treatment system 1 is designed for an electrolytic cleaning concept, in which the component needing treatment is charged, in a purposeful and localized manner, with a specific, suitably chosen treatment liquid and then, a current flow through the component needing treatment and the treatment liquid is generated. For this purpose, the treatment system 1 comprises a media cannula 2, in which the treatment liquid is carried and can be supplied via an outlet opening 4. The end area of the media cannula 2 is of an elongated design, so that a purposefully localized and controlled supply of the treatment liquid is possible. On the media side, the media cannula 2 is connected via a connection hose 6 with a reservoir 8 for the treatment liquid.

In addition, the treatment system 1 is specifically configured as an electric system. As a design principle, it is in particular provided to enable a charging of the medium carried in the media cannula 2, in particular of the treatment liquid carried therein, with current, in particular, with current impulses. The treatment system 1 is configured according to the design principle that the electric current can be fed to the component needing treatment and that the latter can be used as an electrode. For this purpose, the treatment system 1 comprises a conduction element 10 forming an electric current path. In the exemplary embodiment, said conduction element 10 is designed in the manner of a "conventional" electrode, i.e. in particular as an electrically conductive needle-like element made of metal. The outsides of the conduction element 10 are provided with an electric insulation and has only at its free end 12 an exposed metallic contact tip 14. In operation, the latter can suitably be pressed against the component needing treatment, thus establishing an electric contact with said component. Electrically, the conduction element 10 is connected with one of the poles of an electric supply unit 16, in particular a current or voltage source.

A control unit 18, via which the current supplied or the voltage supplied can be controlled and adjusted, is associated with the electric supply unit 16. In addition, the control unit also acts upon a conveying system, not shown in detail, of the connection hose 6, with which the flow rate of the treatment liquid through the connection hose 6 can be adjusted.

To form an opposite pole or the counterelectrode, it is provided to utilize the electric conductivity of the treatment liquid carried in the media cannula 2. For this purpose, the interior of the media cannula 2 is, for its part, electrically connected, via a cable 19 which is connected with the interior of the media cannula 2 in an electrically conductive manner, with the other pole of the electric supply unit 16. Thus, the outlet opening 4 of the media cannula 2 forms in electric terms a contact or an electric contact point, via which the current flow into the component needing treatment is effected. By suitably positioning the media cannula 2 and its outlet opening 4, if possible, in the immediate vicinity of the component needing treatment and by using the outlet opening as an electric contact, it is achieved that the electric current applied for the purpose of treatment and cleaning can flow through the surface zone of the component needing treatment, afflicted by the bacteria, and, from there, as directly as possible, i.e. in particular without making any "detours" through further body tissue or the like, to the outlet opening 4 serving as a contact surface. Therefore, the media cannula 2, inclusive of the electrically conductive treatment liquid carried therein and the corresponding connection elements, form in the exemplary embodiment a second conduction element, forming an electric current path to the outlet opening 4.

The media cannula 2 is made of a suitably chosen electrically insulating basic material, for example, a synthetic material. In order to further promote the utilization of the treatment liquid present in the media cannula 2 as an electric conduction element and to guarantee in particular a reliable electric contacting, the inside of the media cannula 2, i.e. the inner surface facing towards the treatment liquid, is, however, provided with an electrically conductive coating.

Figure 2:
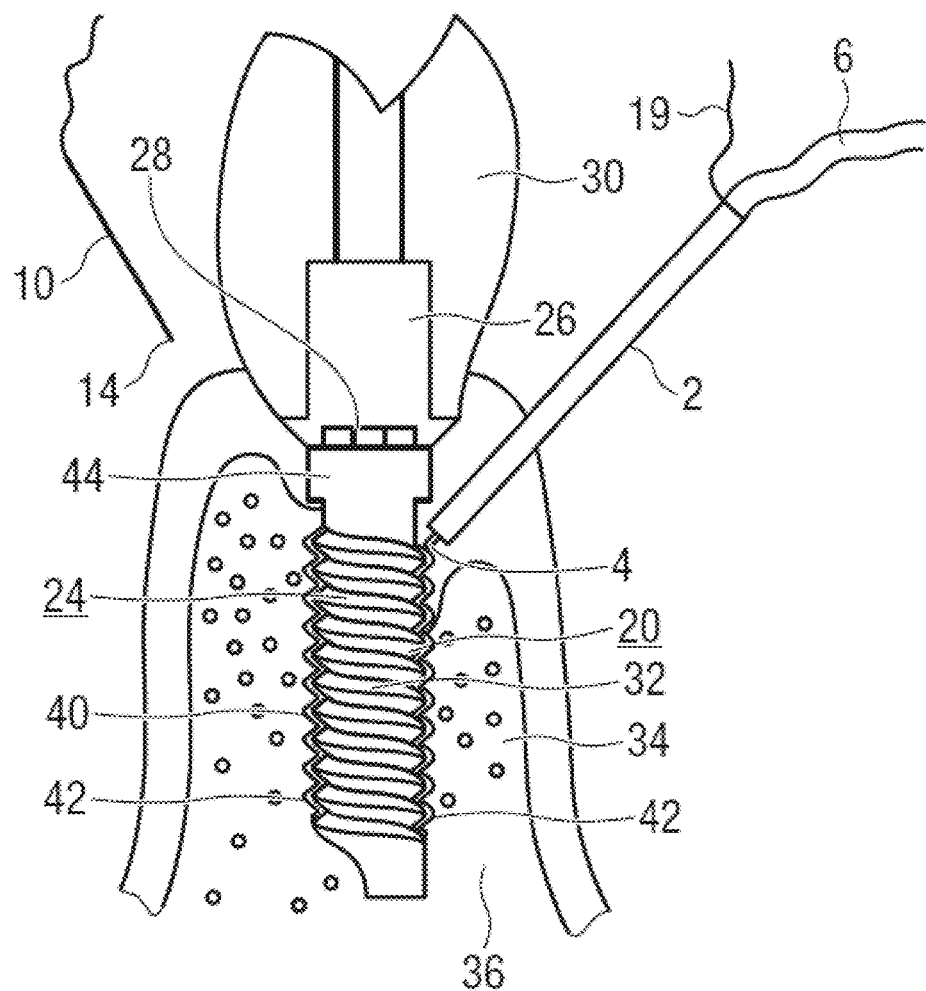
FIG. 2 is an enlarged detail of the treatment system of FIG. 1, Identical parts are marked with the same reference numbers in all figures.

As can be seen from the enlarged representation according to FIG. 2, the media cannula 2 is designed for feeding the treatment liquid to the component needing treatment in a purposeful and localized manner. This component shall then be used, for its part, as an electrode and shall be contacted via the conduction element 10. However, the component needing treatment is a ceramic body 20, which in the exemplary embodiment is designed as a post part 22 of a dental implant 24, inserted into a patient's mouth bone. But, of course, other embodiments are also imaginable, in which a ceramic body, for example a bone implant of any construction or a prosthetic component, for example a superstructure part of a dental implant, shall be cleaned in a flexible and focused manner from the contamination with a biofilm.

In the exemplary embodiment, the dental implant 24 comprises, in addition to the post part 22, a superstructure part 26, which can be fixed on the post part 22 by means of a connecting screw 28 and which carries a denture piece 30. Of course, the dental implant 24 could instead also be of a single-piece design, with the post part 22 and the superstructure part 26 being component parts of one and the same base body. FIG. 2 also shows a spatially limited space area 34, adjacent to the post part 22 in the area of its external thread 32, in the jawbone 36, which is afflicted by periimplantits and correspondingly infested with bacteria.

In general, dental-implant systems, in particular also two-part implant systems, present the problem that inflammations or inflammation focuses may arise due to a penetration of bacteria or germs into the tissue area near the place of insertion, in particular in the area of the external thread 32 cut into the jaw. Such inflammations, in particular also as a consequence of a so-called periimplantitis, may lead to a serious deterioration of the tissue and the bone in the area of the place of insertion, especially when they are able to develop and take hold over a long period. Without suitable countermeasures, these deteriorations may lead to the necessity to remove the entire implant system from the bone and replace it by another prosthetics. This most undesirable effect caused by the periimplantitis may, therefore, lead to a total loss of the implant system, so that renewed surgical measures, such as, for example, scraping out the afflicted area in the jawbone and treatment with a new implant system might become necessary. Such a removal may, furthermore, entail a loss of bone or other loss of tissue substance, which in the extreme case may even make a new treatment with another implant completely impossible. Such a necessity of a new treatment caused by a periimplantitis may occur even after relatively long periods after the first insertion of the implant system of, for example, up to several years or even decades.

The germs or bacteria observed in connection with a periimplantitis may in principle colonize the inside of the components of the dental implant 24, but, as a rule, they preferably adhere directly on the surface of the post part 22 inserted into the jawbone 36, in the contact area with the surrounding tissue or bone material, i.e. in particular in the area of the external thread 32. In the area of the latter, the surface of the post part 22 can be provided with a roughening or the like, in order to particularly promote the growing-in of the tissue or the bone and to support the healing-in of the post part 22 after its insertion. Especially in the area of such a roughening of the surface, actually considered as particularly favorable for the implant system, however, the colonization of germs or bacteria may take place increasedly, the roughness making a specific removal of the existing germs or bacteria even more difficult.

Therefore, suitable countermeasures are urgently required, in order to be able, in case of a beginning or already existing periimplantitis and under preservation of the already inserted implant system, to efficiently combat the inflammation focus and to kill the germs that have penetrated, so that afterwards, sound tissue or sound bone substance can develop again in the area around the external thread 32. For this purpose, it is desirable, in addition to a specific killing of the germs or bacteria in the afflicted area, to also reliably remove their material residues and fragments from the space area concerned, so that then, the afflicted area can be filled again by sound tissue or bone material and an intimate connection between the outer surface of the post part 22 and the surrounding tissue or bone material can develop again. In addition, the biofilm formed by the bacteria layer, including the organic residues of killed bacteria, should reliably be removed.

For this purpose, i.e. for killing germs or bacteria in the insertion area of the post part 22 and in particular also for subsequently rinsing, removing and carrying away the residues of tissue and material of the killed bacteria, the treatment element 1 is provided. With regard to its design and fundamental configuration, the treatment element 1 is based on two main concepts, each of which is independently considered as inventive: on the one hand, it is designed for specifically killing the germs or bacteria present in the insertion area of the dental implant 24 through specifically feeding a cleansing agent or disinfectant which is bactericidal, but tolerated by the human organism. On the other hand, it is designed for removing any residues or fragments of germs and/or bacteria still adhering on the surface of the post part 22, in particular in the area of the external thread 32, through a suitable charging with current of current impulses, from the outer surface of the post part 22, so that such residues can then be washed out.

In a first aspect, which is independently considered as inventive both with regard to the configuration of the system and with regard to the provided steps of the treatment method, the treatment system 1 is, therefore, designed, both structurally and functionally/conceptually, for specifically feeding the treatment liquid for killing the germs or bacteria and/or for cleaning the inserted implant part into the insertion area of the post part 22, in particular the area of the latter's external thread 32.

In a second aspect, which is also independently inventive both with regard to the configuration of the system and the choice and composition of the basic constituents of the utilized treatment liquid and with regard to the provided steps of the treatment method, the treatment system 1 is designed for reliably detaching the killed bacteria or germs, respectively their residues or fragments, from the outer surface of the post part 22, so that they can then be washed out and, afterwards, sound tissue or bone material can again get into contact with the surface of the post part 22 and the latter can again grow completely into sound tissue or bone material. For detaching the bacteria or germs, respectively their residues or fragments, from the surface, it is provided to wet the latter with a conductive treatment liquid, charging it with current. It has also turned out most surprisingly that exactly this pulsed charging with current, in combination with suitably chosen ion concentrations in the treatment liquid, seems to effect the detachment of the bacteria or germs, respectively their residues or fragments, from the surface underneath in a particularly reliable manner, even if said surface is roughened and, in fact, particularly promotes the adhesion of organic material due to its surface structure.

This is based on the surprising discovery that the charging of the post part 22 with current, using a suitably chosen treatment liquid, in the area of the outer surface of the post part 22, i.e. in particular in the area of the external thread 32, leads to an electrolytic reaction in the treatment liquid and, thus, possibly to the generation of gas bubbles in the immediate vicinity of the surface. Through this formation of gas bubbles on the surface of the post part 22, the superficially adhering components or fragments of the germs or bacteria are also detached and completely removed, so that they cannot offer a basis or a nutrient medium for a new colonization of germs in these areas. What remains is a roughened and porous surface, cleaned from germs, bacteria or their components or residues, of the post part 22, which can serve well as a basis for a future integration into the regrowing bone tissue.

It is, however, necessary for such a treatment concept, that the post part 22—or the component needing treatment in general—can be used as an electrode in the treatment system 1. The ceramic body 20 constituting the post part 22 is specifically suitably designed for that. To make this possible, the ceramic body 20 has in its surface area 40 intended for the contact with human tissue a sufficiently high electric conductivity and, therefore, a sufficiently low specific electric resistance of maximally $10^{-2}$ Ωcm, preferably of maximally $10^{-5}$ Ωcm.

Several embodiments of the ceramic body 20 can be taken into consideration for specially providing this electric conductivity. On the one hand, the complete dental implant 24, or at least its post part 22, could be made completely of an electrically conductive or an electrically semiconductive ceramic, which can then be electrically contacted for cleaning purposes either occlusally or via the interior. Of course, it is also possible to use an electric contacting via the media cannula 2 from outside.

Alternatively, it is also imaginable to add an electrically conductive or semiconductive material, preferably based on ceramic and/or carbon, to a non-electrically conductive ceramic which is suitable as an implant module, to produce an electric conductivity or electric semiconductivity.

As a further alternative, the dental implant 24 or its post part 22 can be designed as a fully ceramic, non-electrically conductive ceramic body 20, as provided in the exemplary embodiment. In order to guarantee, nevertheless, the desired electric conductivity in the surface area 40, the latter is provided with an electrically conductive or electrically semiconductive coating 42. This coating 42 can be applied completely/on the entire part or only in partial area of the surface of the post part 22; in the exemplary embodiment shown, it is applied on the post part 22 only. Of course, it is also possible—depending on the intended use—to provide other components, such as, for example, the superstructure part 26 provided as the prosthetic component, completely or partially with the coating 42. In the exemplary embodiment, the implant shoulder 44 is provided for the electric contacting. In the area of said implant shoulder 44, the coating 42 has a greater thickness, e.g. two, five, ten times the thickness of the coating 42 in the remaining surface area 40. If the outside as well as the inside of an implant would be coated in such a manner, an electric contacting would also be possible via the inside of the implant.

The post part 22 is designed as a ceramic body 20 based on yttrium-oxide-stabilized and/or aluminium-oxide-stabilized zirconium oxide. In addition, its surface area 40 intended for the contact with human tissue is provided, at least in a partial area, with a structure including nanoscopic pores or with a structure otherwise nanoscopically configured, and has a depletion zone based on yttrium-oxide-stabilized and/or aluminium-oxide-stabilized zirconium oxide with a reduced share of yttrium oxide or aluminium oxide, as compared with the inner volume The coating 42 can be formed by a metal, by an electrically conductive synthetic material and/or by an electrically conductive carbon. In the exemplary embodiment, however, the coating 42 is formed by a doped ceramic, preferably indium oxide and/or indium-tin oxide, zinc oxide, silicon nitrite, $MoSi_2$, $Si_3N_4$—$MoSi_2$—$SiC$, $ZrO_2/CaO$, $Al_2O_3/TiN$, $BaTiO_3$, a silicide, a nitride, a ceramic containing titanium, and/or a titanate.

Such an electrically conductive coating 42 can be advantageous even for dental implants which, by themselves, are metallic. In the case of an anodic switching of titanium implants, in particular made of titanium grade IV or purer titanium, a titanium-oxide layer will form, which directly after its formation will very greatly reduce or prevent the electrochemical processes on the surface, unless the electric voltage is increased. Therefore, an anodic energization for cleaning purposes is possible for a very short time or a single time only without endangering the patient through the electric voltage. If such a titanium implant is coated with an electrically conductive or electrically semiconductive ceramic, the growth of titanium oxide under anodic energization can be prevented. In this way, it would be possible to use the anodic energization for cleaning the implant surface over a long duration. Another advantage of such a surface would be the fact that no metal ions could be detached from the metallic implant.

A particular promotion of this separation of superficially adhering biofilm components from the inserted post part 22, which is desirable in the sense of a reliable cleaning of the surface, can be achieved through an advantageous, particularly well suited process guidance during the charging with current. Said process guidance can be such that due to the current flow, an electrolytic formation of gas bubbles taking place in the area of the inserted surface is particularly increased. Here, the post part 22 can be switched anodically or cathodically. In particular in case of an at least temporary cathodic switching of the post part 22, hydrogen gas, which contributes in a particularly efficient manner to the formation of gas bubbles, develops through electrolytic induction, whereas, in case of an anodic switching of the post part 22, depending on the composition of the treatment liquid, chlorine gas, oxygen, nitrogen, carbon monoxide and/or carbon dioxide develop. The gas bubbles forming thereby rise in the surrounding liquid and thus generate entraining effects, through which the above-mentioned surface components are also removed and discharged towards the outside. It was, for example, most surprisingly observed that, when using a solution containing positive ions, for example, an aqueous saline solution, these ions deposit on the post part 22 when the latter is cathodically switched and, thus, clearly increase the formation of gas bubbles. For example, the presence of Na+ ions in case of a cathodic switching of the post part 22 leads to a considerable formation of gas bubbles, because Na+ reacts with the surrounding water and forms NaOH, releasing hydrogen.

In another independent inventive aspect, also both with regard to the configuration of the system and with regard to the provided steps of the treatment method, the treatment system 1 is designed for a particularly simple and efficient combination of the before-mentioned aspects. This is based on the concept that both the provided feeding of the cleaning liquid and the specific detachment of the residues and fragments of bacteria and germs can be achieved by applying the above-mentioned current impulses in a common system and, thus, with particularly simple means.

The treatment liquid used is suitably chosen and composed in view of these aspects. Choice and composition of the basic constituents of the treatment liquid are chosen in particular in view of the intended function, i.e. application of an electric current in the space area of the surface needing treatment, it being in particular ensured that the electric conductivity of the treatment liquid is sufficiently high for this purpose. This shall be ensured in particular by a chosen sufficiently high ion density in the treatment liquid. For this purpose, a metallic salt, preferably in aqueous solution, is provided as a basic constituent of the treatment liquid. Said metallic salt supplies the ions for the transport of current and, in addition, the conversion products arising after the respective electrode reaction can also posses suitable biochemical effects. By specifically choosing a sufficiently high electric conductivity, it shall be ensured that during the performance of the cleaning method at the inserted implant the current flows through the treatment liquid and, thus, through the parts and components needing treatment, but not through the patient's body tissue, so that a risk for the patient through an unwanted current flow through soft tissue, bones, blood, and/or other body materials can be minimized. The electric conductivity of the treatment liquid should, if possible, amount to a multiple of the electric conductivity of blood, bones, soft tissue, fatty tissue, or other body materials.

Consequently, the following conductivity values are in particular taken into consideration in the choice and composition of the basic constituents of the treatment liquid (the electric conductivity a being indicated in the usual unit mS/cm):

Skin: 0.03-0.1 mS/cm
Bone: 0.06-0.2 mS/cm
Fatty tissue: 0.20-1.0 mS/cm
Muscular tissue: 0.80-2.5 mS/cm
Blood: approx. 6.7 mS/cm
Other body liquids: approx. 15 mS/cm To keep the risk potential for the patient suitably low and to restrict the current flow to the desired regions, the electric conductivity should, therefore, amount to at least twice, preferably five times, particularly preferably ten times the conductivity of other body liquids. Therefore, the electric conductivity of the treatment liquid should have a value of at least 30 mS/cm, preferably at least 75 mS/cm and particularly preferably at least 150 mS/cm. In comparison with blood, this means that the electric conductivity of the treatment liquid preferably amounts to at least approx. five times, preferably at least approx. ten times and particularly preferably at least approx. twenty times the conductivity of blood. Measurements have shown that, when applying a treatment liquid chosen in this way, the electric voltage to which the body tissue, the blood, the body liquids, etc. are exposed, is lower than 6 V, preferably lower than 3 V, particularly preferably lower than 1.5 V, so that damages for the patient can securely be excluded, as the voltages are kept low. To achieve such a conductivity, in particular the ion concentration in the treatment liquid and in the basic constituents forming the latter are chosen sufficiently high; for this purpose, caustic solutions, acids, salts, and/or other ion-forming substances or compositions of matter can be used.

Choice and composition of the basic constituents of the treatment liquid take into consideration to a particularly high degree that the cleaning or biofilm-detaching effect of the electrolytic treatment of a contaminated implant surface is based on a combination of several causes, which should be made use of, if possible, complementarily to each other. On the one hand, gases or gas bubbles may form, when the current flows through the electrolyte, preferably in the area of the electrodes, which gases or gas bubbles have a detaching (mechanical) effect on the biofilm. These gases develop immediately at the implant surface serving as an electrode and, thus, between said implant surface and the biofilm. The growth rate and maximum size of the developing gas bubbles influence the detachment process.

The second reason for the implant-cleaning or biofilm-detaching effect of the electrolytic process is the decomposing, destroying, and dissolving effect of the electrolytically created substances or compositions of matter on the adhesion of the biofilm on the implant surface, i.e. on the gluing or anchoring mechanism.

The third reason for the cleaning or detaching effect of the electrolytic process is based on material-eroding effects on the implant material, through which component parts or particles of the implant properly speaking are extracted therefrom in its surface area.

The fourth reason for the cleaning or detaching effect of the electrolytic process is based on the formation of an oxide layer of metallic implants, which allow this. In this case, metal atoms of the metallic basic material penetrate the possibly already existing oxide layer due to the applied electric voltage and react with substances of the electrolyte (mostly oxygen=>formation of metal oxide). In metals which do not form an oxide layer or do not form a mechanically stable oxide layer, non-oxidic compositions of matter (mostly salts) may also arise, which then get into solution.

The basic constituents provided for forming the treatment liquid are suitably chosen and combined with each other in view of these effects. Furthermore, it is taken into account as a fundamental design target that no toxic effects or effects which are hazardous or disagreeable to a patient in another manner should occur, so that the treatment liquid is also suitably for being applied on the inserted dental implant, i.e. in the patient's mouth. In the exemplary embodiment, the basic constituents provided are at least one salt, on the one hand, and one acid, on the other hand, preferably diluted with water, whose choice and composition depends in particular on the above-mentioned criteria. It is particularly preferable to provide, as an acid, phosphoric acid, citric acid, formic acid, ethanoic acid, lactic acid, carbonic acid, or a combination thereof. Alternatively or additionally, it is particularly preferable to provide, as a salt, sodium, calcium, aluminium, magnesium, tin, or potassium iodide, chloride, nitrate, carbonate, or hydrogen carbonate, and/or ammonium chlorite, nitrate, or iodide, or a combination thereof.

The post part 22 is preferably switched cathodically during the treatment with the treatment liquid. In this case, positively charged ions (cations) wander to the surface of the post part 22. These ions can be in particular $H^+$ ions, metal ions or long-chain hydrocarbon ions, e.g. from ionic liquids. The salt provided as a basic constituent for the treatment liquid is in this case particularly purposefully chosen in view of the properties of the cations which shall promote the above-mentioned process or make it possible in the first place. To generate as high an electric conductivity as possible, small ions ($H^+$ ions or metal cations) are particularly suitable, which, in addition, in the manner of another particularly favorable effect, are able, in a relatively easy manner, to penetrate the possibly existing biofilm. $H^+$ ions are reduced to elementary hydrogen H on the cathode formed by the post part 22. This generates a formation of bubbles.

Alkali metals, alkaline earth metals and/or aluminium react on the cathode with the surrounding water and form elementary hydrogen and its metal cations and $OH^-$ ions. This means that hydrogen bubbles and the hydroxide of the used metal ions form. Through the combination of these components, it is, therefore, achieved, in addition to the detaching effect of the arising hydrogen, that the metal hydroxide has an antibacterial effect and a diluting or dissolving influence on the biofilm or the latter's adhesion mechanism.

To avoid incompatibilities with the body tissue, in particular the metal cations produced naturally in the body (e.g. potassium and/or sodium ions) are particularly preferred as metal cations. Furthermore, calcium, magnesium and/or aluminium ions are also suitable. The salt provided as a basic constituent for the treatment liquid is, therefore, particularly preferably a salt of these metals, in particular because these metal cations can anyhow exclusively be made available in the form of a salt, e.g. dissolved in water.

These metallic salts can be compounds of the above-mentioned metals with a suitable halogen, for example with sulphur, phosphor, nitrogen, fluorine, chlorine, iodine, bromine, hydrocarbon, oxygen, boron, or other nonmetals. The halogen is advantageously suitably chosen considering the principle "the larger the anion, the lower the electric conductivity" and in view of the generally desired high electric conductivity. Furthermore, preferably only substances influencing neither health nor the periimplantary tissue are taken into consideration as anion. Furthermore, it has to be taken into account that disagreeable smells or taste compounds are unwanted. For these reasons, sulphur anions or anions containing sulphur in combination with oxygen or other elements are considered as rather unsuitable. This also applies to fluorine, bromine, nitrogen, and boron ions, possibly also in combination with other elements.

In contrast to that, phosphates, phosphate ions and hydrogen phosphate ions mostly have hardly any detrimental effect or none at all. Chlorine ions or ions containing chlorine mostly have an antibacterial effect. Should the chlorine ion, however, be electrolytically oxidized and be present in water in the elementary state, hydrochloric acid and hypochlorous acid will form. It is true that, in combination with the cathodically generated hydroxide, this would lead to a neutralization, but examinations have shown that the chlorine arising on the counterelectrode to the implant (anode) escapes from the electrolyte to a great extent in the form of gas. If it is not possible to suck off the chlorine completely during the treatment, severe cauterizations in the lungs and/or the mucous membranes may result. In this case, one has to balance whether the benefit for the patient or the latter's endangerment is greater.

With regard to the phosphates of aluminium, potassium, sodium, calcium, or magnesium, it must, furthermore, be noted that their dissolubility in water is so low that a sufficient electric conductivity of the electrolyte is not guaranteed (these phosphates are, however, very well suited as additives of the electrolyte for buffering the pH-value). Although chlorides of the four above-mentioned metals would have a sufficient dissolubility in water and a good cleaning and killing effect on the biofilm, they cannot be considered as the optimum. In case of nitrates and/or nitrites, an endangerment of the patient through the formation of $NO_x$ gases has to be expected. For this reason, the use of nitrites or nitrates is not advisable.

In view of the above-mentioned design targets, in particular for a particularly good compatibility for the patient, iodine is provided in a preferred embodiment as halogen. It is particularly advantageous that iodine salts of potassium and of sodium are naturally present in the human body. Through the oxidation of iodine ions on the anode, first of all elementary iodine develops, which can dissolve in a sodium-iodide/potassium-iodide solution. An iodine-potassium-iodide solution or an iodine-sodium-iodide solution will result thereby. Both solutions are strong disinfectants, which have proved themselves in human medicine.

Pure solutions of sodium iodide or potassium iodide or a mixture of the two entail, however, the possible disadvantage of the formation of sodium hydroxide and/or potassium hydroxide and the resulting increase of the pH-value. It could, in fact, quite generally, be considered as a problem of the above-mentioned formation of metal hydroxide that a metal hydroxide increases the pH-value of the electrolyte. Such an increased pH-value and the developing caustic solution of the dissolved metal hydroxide might have an undesired influence on the surrounding tissue in the patient's mouth and in particular, on the bone. Furthermore, adjacent teeth might be damaged. Furthermore, the formation of hydroxides might lead to their precipitation on the post part 22 or generally on the component part needing treatment, due to their very low water solubility, thus impeding the further current flow and, thus, the process as a whole. At best when using a calcium salt in the treatment liquid, the developing calcium hydroxide, which is present in the bone material, could be integrated into the bone; calcium is, therefore, a particularly preferable constituent of the salt. To compensate these undesired influences, the treatment liquid contains the acid as another basic constituent in the manner of a pH-buffer or pH-reducer.

The acid, for its part, is chosen, in the manner of a design criterion, in such a way that it does not endanger, if possible, the patient or the periimplantary tissue, but, on the one hand, neutralizes the hydroxide (and prevents, if possible, an increase of the pH-value to more than 7), whereby, on the other hand, the reaction products should serve for the actual target of cleaning the implant body and removing the biofilm. As mineral acids, phosphoric acids and/or phosphate acids are preferred for that purpose. For reasons of hazards to health and/or to the bone/tissue, their concentration should be limited. A particularly preferable acid, which is also considered as a mineral acid and which has a particularly positive effect on the overall target of killing and cleaning, is, on the other hand, carbonic acid. The usable quantity of the latter is, however, limited through its relatively low solubility in water.

Contrary thereto, organic acids, similar to mineral acids, provide pH-value-reducing and hydroxide-neutralizing $H^+$ ions. As, in addition, they do not produce any damages, or at most slight damages, in the tissue or in the patient as a whole, such organic acids are most particularly preferred as a basic constituent of the treatment liquid. Organic acids are, for example, alkane acids, fruit acids, carboxylic acids as well as hydroxy carbonic acids. α-hydroxy carbonic acids have turned out to be particularly suitable acids. In particular, the particularly preferable acids lactic acid, citric acid, and malic acid have no effects hazardous to health on the patient in general or on the periimplantary tissue. Especially on implants greatly covered and contaminated with a biofilm, on which tartar has also developed, a good cleaning success was achieved with relatively low dosages of ethanoic acid. Other acids, which have the cleaning as well as the bactericidal effect, but, for health reasons, are not harmless, would be fumaric acid, gluconic acid, glycolic acid, salicylic acid, mandelic acid, tartaric acid, oxalic acid, and formic acid.

When the hydroxide ion $OH^-$ is neutralized with the corresponding $H^+$ ion of an acid, the metallic salt of the acid of the corresponding metal hydroxide will additionally be produced. The intended use of the acid is, therefore, not only advantageous for buffering the pH-value, but, in addition, contributes to the conversion of the relatively little water-soluble hydroxide into relatively well water-soluble salts, thus preventing the precipitation of unwanted deposits, detrimental to the process, on the component part needing treatment. The above-mentioned salts are in particular used when combining the above-mentioned preferred materials, among other, also in the field of medicine. During the neutralization of the potassium, sodium and/or calcium hydroxide with lactic acid, potassium lactate (possessing a broad-spectrum antimicrobial effect), sodium lactate or calcium lactate arises. It, however, the produced hydroxides are neutralized with citric acid, citrates of potassium, sodium or calcium will arise. Especially in the case of sodium citrate, this is particularly advantageous, as it prevents blood coagulation. This is particularly advantageous, because blood escaping during the process and coagulating on the implant surface might impede the ion wandering to the implant surface and, thus, the continuation of the treatment process as a whole.

Contrary thereto, in case of a neutralization of the hydroxides with malic acid, malates of the respective cation arise, which also have favorable effects on the process. in case of a neutralization of the hydroxides with ethanoic acid, acetates of potassium, sodium and/or calcium arise, which also have a favorable effect on the process.

Lactates, citrates, malates, and/or acetates of potassium, sodium and/or calciums all possess an acid-regulating effect and are so compatible that according to the present EU regulations concerning food additives, their use is not subject to any quantitative limitation.

When using acids in the electrolyte in combination with iodides and/or chlorides of sodium, potassium, magnesium, aluminium, and/or calcium, it has surprisingly turned out in the electrolytic application that the direct reduction of the $H^+$ ions influences the formation of bubbles so positively that the biofilm comes off clearly more quickly and better. At a high generation rate, a multitude of relatively small bubbles develop, which due to their relatively small size are able to detach the biofilm as a whole and not only locally from the surface underneath it. In this way, the biofilm is preferably detached as a whole or in relatively large coherent pieces instead of a multitude of smaller fragments, which entails a clearly improved cleaning effect.

Instead of metal cations, ammonium cations can also be used. In this case, there exists, however, the risk that in the electrolytic process, other ammonium compounds (e.g. ammonia) are generated. This constitutes a risk for the patient and is also perceived through a very disagreeable taste and smell.

It was observed in tests that the biofilm comes off partially in very small fragments or else in larger coherent pieces. The latter is preferred, because in this case, very favorable cleaning results can be achieved on relatively large areas. Examinations have also shown that the removal of the detached biofilm and/or its fragments is promoted by a formation of foam on the implant surface. It has turned out that it is favorable to apply, after the use of an electrolyte consisting of the above-described metal salts, acids and water, responsible in particular for killing and detaching, a second electrolyte, which shows in addition a formation of foam in the area of the cathode. Such a formation of foam can be achieved by preferably adding to the electrolyte another substance comprising at least three $CH_2$ chain links or at least one $CH_2$ chain link and at least one carbon ring compound. Here, e.g. oil and/or chlorhexidine can be used. Furthermore, ionic liquids, which preferably contain $I^-$, $Cl^-$ and/or $OH^-$ ions, can also be used. As the organic cation share of an ionic liquid is under certain circumstances reduced on the implant surface and remains there, it is possible in a particularly favorable embodiment, to add bone-growth factors to this cation share.

If chlorides and iodides are mixed in the correct ratio, the disturbing formation of chloric gas can be avoided. At the anode, the following is generated:

$$2J+5Cl+6H_2O \rightarrow 10HCl+2HIO_3$$

This means that both hydrochloric acid and iodic acid are formed at the anode. These acids certainly have a strong antimicrobial effect and are also neutralized again when meeting with the cathodically produced hydroxide.

A most particularly preferred composition of the treatment liquid, which in the laboratory test showed particularly favorable cleaning properties, comprises an aqueous solution of sodium iodide (NaI) or potassium iodide (KI) in a mixing ratio of at least 5 g, preferably at least 10 g, particularly preferably at least 20 g of the salt per 30 ml liquid (i.e. water $H_2O$, possibly enriched with $CO_2$), buffered, by the addition of lactic acid, to a pH-value of approx. 2.7 to 2.9.

In the process guidance, a mean current density at the post part 22 or at the component part needing treatment of at least 50 mA/cm$^2$, advantageously of at least 100 mA/cm$^2$, particularly preferably of at least 250 mA/cm$^2$, is provided, this current density being referred to the outer surface of the post part 22 (i.e. without taking into account any surface-enlarging properties, such as, for example roughness or surface structure). For the detachment of the biofilm, a mean current density of 50 mA/cm$^2$ to 300 mA/cm$^2$, advantageously of 100 mA/cm$^2$ to 200 mA/cm$^2$, has turned out to be particularly favorable. For the removal of the biofilm fragments, the mean current density should preferably be increased to the range of 300 mA/cm$^2$ to 5,000 mA/cm$^2$ or particularly advantageous of 1,000 mA/cm$^2$ to 2,000 mA/cm$^2$.

The treatment system 1 and in particular its control unit 18 is designed for a coordinated process control in the sense that the feeding of the treatment liquid, on the one hand, and the charging with current, on the other hand, can be effected in a manner adapted to each other. For this purpose, it can, for example, be provided to effect via the control unit 18 a coordinated activation of the conveying unit for the treatment liquid, associated with the connection hose 6 or the reservoir 8, on the one hand, and the electric supply unit 16, on the other hand.

LIST OF REFERENCE NUMBERS

1 Treatment system
2 Media cannula
4 Outlet opening
6 Connection hose
8 Reservoir
10 Conduction element
12 End
14 Contact tip
16 Supply unit
18 Control unit
19 Cable
20 Ceramic body
22 Post part
24 Dental implant
26 Superstructure part
28 Connecting screw
30 Denture piece
32 External thread
34 Space area
36 Jawbone
40 Surface area
42 Coating
44 Implant shoulder

The invention claimed is:

1. A bone implant comprising a dental implant (24) having a ceramic body (20), with an outer surface area (40) comprising a doped ceramic having an electrically conductive synthetic material, an electrically conductive carbon, or both, and said outer surface area (40) having a specific electric resistance of maximally $10^{-2}$ $\Omega$cm.

2. The bone implant of claim 1, wherein the outer surface area (40) has a specific electric resistance of maximally $10^{-4}$ $\Omega$cm.

3. The bone implant of claim 1, wherein the outer surface area (40) is an electrically conductive coating (42).

4. The bone implant of claim 3, wherein the electrically conductive coating (42) comprises a doped ceramic.

5. The bone implant of claim 1, and further comprising a superstructure part (26) and wherein the ceramic body (20) is a post part (22) which can be anchored in a jawbone (36).

6. The bone implant of claim 5, and further comprising an implant shoulder (44), said implant shoulder (44) and the outer surface area (40) each have an electrically conductive coating, wherein the electrically conductive coating on the implant shoulder (44) is thicker than the electrically conductive coating on the outer surface area (40).

7. The bone implant of claim 5, wherein the post part (22) comprises yttrium-oxide-stabilized zirconium oxide, aluminum-oxide-stabilized zirconium oxide, or both.

8. The bone implant of claim 7, wherein the outer surface area (40) comprises an area having a structure including nanoscopic pores or is nanoscopically configured, and a depletion zone comprising yttrium-oxide-stabilized zirconium oxide, aluminum-oxide-stabilized zirconium oxide, or both, with a reduced share of yttrium oxide or aluminum oxide as compared with the inner volume.

9. The bone implant of claim 1, wherein the outer surface area (40) has a specific electric resistance of maximally $10^{-5}$ $\Omega$cm.

10. The bone implant of claim 3, wherein the electrically conductive coating (42) comprises at least one of indium oxide, indium-tin oxide, zinc oxide, silicon nitrite, $MoSi_2$, $Si_3N_4$—$MoSi_2$—$SiC$, $ZrO_2/CaO$, $Al_2O_3/TiN$, $BaTiO_3$, a silicide, a nitride, titanium, and a titanate.

11. The bone implant of claim 1, wherein the outer surface area (40) is a surface of the ceramic body (20).

* * * * *